United States Patent [19]

Bonacina et al.

[11] Patent Number: 5,512,247
[45] Date of Patent: Apr. 30, 1996

[54] APPARATUS FOR TESTING PIPETTING NEEDLE LINEARITY IN AN AUTOMATED ANALYZER

[75] Inventors: Guido Bonacina, Emmenbrücke; Thomas Caratsch, Reutlingen; Rolf Moser, Vitznau, all of Switzerland

[73] Assignee: Hoffmann-La Roche Inc., Nutley, N.J.

[21] Appl. No.: 420,279

[22] Filed: Apr. 11, 1995

[30] Foreign Application Priority Data

May 2, 1994 [CH] Switzerland ............. 1382/94

[51] Int. Cl.⁶ .................................................. G01R 31/00
[52] U.S. Cl. ...................... 422/67; 422/63; 422/64; 422/82.01; 422/82.02; 422/100; 436/49; 324/519; 324/661; 324/758
[58] Field of Search .............................. 324/519, 661, 324/758; 422/82.01, 63, 64, 67, 100, 82.02; 436/49; 201/401

[56] References Cited

U.S. PATENT DOCUMENTS

| | | | |
|---|---|---|---|
| 4,757,437 | 7/1988 | Nishimura | 73/864.25 |
| 4,830,832 | 5/1989 | Arpagaus et al. | 422/63 |
| 5,055,263 | 10/1991 | Meltzer | 422/63 |
| 5,104,621 | 4/1992 | Pfost et al. | 422/63 |
| 5,270,210 | 12/1993 | Weyrauch et al. | 422/100 |
| 5,306,510 | 4/1994 | Meltzer | 422/63 |

FOREIGN PATENT DOCUMENTS

| | | |
|---|---|---|
| 9116675 | 10/1991 | European Pat. Off. . |
| 555739 | 8/1993 | European Pat. Off. . |
| 91/16675 | 10/1991 | WIPO . |

OTHER PUBLICATIONS

Derwent Abstract No. AN-93-260036/33.

Patent Abstracts of Japan, vol. 14 (498) (P-1124) (Oct. 30, 1990) of JP-A-02 203 269.

Primary Examiner—Jeffrey R. Snay
Assistant Examiner—Sharidan Carrillo
Attorney, Agent, or Firm—George M. Gould; George W. Johnston; John P. Parise

[57] ABSTRACT

An analyzer has a horizontally disposed baseplate on which primary containers and secondary containers are disposed, a pipetting needle, a transport device, and a control device. The pipetting needle is formed of an electrically conductive material and is connected to a metering device by a tubing, and is for transferring a predetermined volume of liquid each time from a primary container to a secondary container. The transport device is for the controlled transport of the pipetting needle in three directions at right angles to one another, two of the transport directions extending horizontally and the third transport direction extending vertically. The control device is for controlling the metering device and the transport device. For the purpose of testing the linearity of the pipetting needle the analyzer includes a device for guiding the tip of the pipetting needle around the periphery of the top edge of a reference body (the tip of the pipetting needle is guided at a specific distance from the top edge of the reference body, which distance is a measure of the acceptable curvature of the pipetting needle), and an electrical circuit for detecting electrical contact between the tip of the pipetting needle and the reference body.

5 Claims, 12 Drawing Sheets

APPARATUS FOR TESTING PIPETTING NEEDLE LINEARITY IN AN AUTOMATED ANALYZER

BACKGROUND OF THE INVENTION

1. Field

The apparatus and method of the present invention relate to the field of analyzers having automated pipetting capability, and more particularly, to analyzers capable of testing the linearity of the pipetting needle.

2. Description

Experience has shown that during operation of an automatic pipetting device, deformation of the pipetting needle can occur due to mechanical loads placed upon the needle, for example, by the intended use of the pipetting needle for piercing sample container lids or reagent container lids for the withdrawal of samples or reagents, or by inaccurate positioning of the pipetting needle. Although a very slight curvature of the pipetting needle is usually acceptable (some tolerance is provided for positioning the pipetting needle at the various pipetting positions), if the curvature of the pipetting needle is greater than the permissible tolerance, such curvature may result in malfunction of not only the pipetting device, but also the entire analyzer. Such malfunction can occur hours after the analyzer has begun operation and may cause damage (such as loss of samples and reagents) and expense, including repair costs by the user or an external service, and other expenses resulting from the breakdown of the analyzer.

When automatic pipetting devices of the above kind are used, it is desirable to test the linearity of the pipetting needle by a reliable method, for example, after adjustment of the pipetting needle transport device and before each operation of the analyzer, thereby allowing the pipetting needle to be replaced before operation, if necessary.

The object of the invention, therefore, is to make available an analyzer and a method of the type indicated hereinbefore which allows for reliable testing of the linearity of the pipetting needle.

According to the invention, the first part of the above problem is solved by an analyzer having:

means for guiding the tip of the pipetting needle around the periphery of the top edge of a reference body, the tip of the pipetting needle being guided at a specific distance d from the top edge of the reference body, which distance is a measure of the acceptable curvature of the pipetting needle, and an electrical circuit for detecting an electrical contact between the tip of the pipetting needle and the reference body.

According to the invention, the second part of the above problem is solved by a method for testing the linearity of the pipetting needle, which is characterized in that:

the tip of the pipetting needle is guided around the periphery of the top edge of a reference body, the tip of the pipetting needle being guided at a specific distance d from the top edge of the reference body, which distance is a measure of the acceptable curvature of the pipetting needle, and any contact between the reference body and the pipetting needle is detected by means of an electrical circuit.

A major advantage of the analyzer and method according to the invention is that it gives very reliable testing of the linearity of the pipetting needle.

SUMMARY OF THE INVENTION

The subject invention provides an analyzer having a base plate, a metering device, a pipetting needle, a transport device, a reference body, and a control device.

The horizontally disposed baseplate has primary containers and secondary containers disposed thereon. The metering device is for measuring a predetermined volume of a liquid. The pipetting needle is for transferring a predetermined volume of liquid from a primary container to a secondary container. The pipetting needle is formed of an electrically conductive material and is connected by tubing to the metering device. The transport device is for the controlled transport of the pipetting needle in three directions at right angles to one another, two of the transport directions extending horizontally and the third transport direction extending vertically. The electrically conductive reference body has a top edge and is positioned at a predetermined location. The control device is for controlling the metering device and the transport device.

The control device has means for guiding the tip of the pipetting needle around the periphery of the top edge of the reference body, and an electric circuit between the pipetting needle and the reference body. The tip of the pipetting needle is guided at a specific distance from the top edge of the reference body. The distance is a measure of the acceptable curvature of the pipetting needle. The electrical circuit between the pipetting needle and the reference body, detects an electrical contact between the tip of the pipetting needle and the reference body.

Also provided is a method of testing the linearity of the pipetting needle in an automatic pipetting analyzer having an electrically conductive reference body with a top edge, and a transport device adapted to move the pipetting needle in three directions at right angles to one another. The method comprises two steps. The first step is guiding the tip of the pipetting needle around the periphery of the top edge of the reference body at a specific distance from the top edge of the reference body. The distance is a measure of the acceptable curvature of the pipetting needle. The second step is detecting any contact between the reference body and the pipetting needle. Contact indicates that the pipette needle has unacceptable linearity.

BRIEF DESCRIPTION OF THE FIGURES

One exemplified embodiment of the invention is described below with reference to the accompanying drawings.

DETAILED DESCRIPTION OF THE INVENTION

Figure 1:
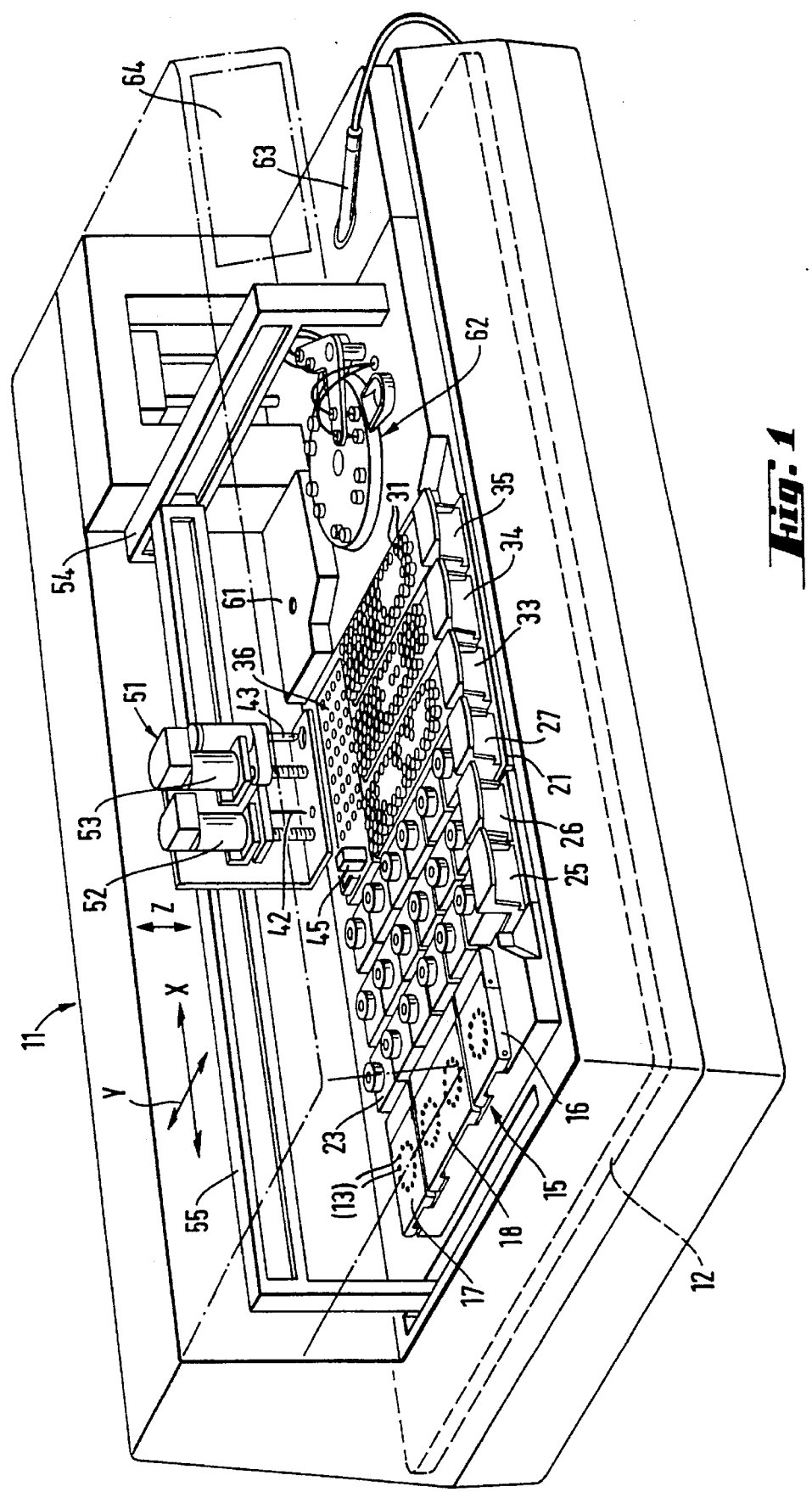
FIG. 1 is a perspective view of an analyzer.

The subject invention will now be described in terms of its preferred embodiments. These embodiments are set forth to aid in understanding the invention, but are not to be construed as limiting.

The invention relates to an analyzer comprising the following components:

- a horizontally disposed baseplate on which primary containers and secondary containers are disposed,
- a pipetting needle having an electrically conductive material and connected to a metering device by a tubing, for transferring a predetermined volume of liquid each time from a primary container to a secondary container,
- a transport device for the controlled transport of the pipetting needle in three directions at right angles to one another (the X, Y and Z directions), two of the transport directions (X and Y directions) extending horizontally and the third transport direction (Z direction) extending vertically, and
- a control device for controlling the metering device and the transport device.

The invention relates more particularly to the construction of the transport device for the pipetting needle of the pipetting device of an automatic analyzer, such as an analyzer for analyzing biological samples.

The invention also relates to a method for the automatic transport of a pipetting needle 42 of an automatic pipetting device of an analyzer to a number of pipetting positions by means of a transport device 51–55, each pipetting position corresponding to the position of a specific container, the transport device 51–55 being adapted to move the pipetting needle 42 in three directions (X, Y, Z) at right angles to one another, each of said directions being parallel to one of the coordinate axes of the coordinate system of the transport device 51–55.

A typical pipetting operation in an automatic analyzer is removal of a specific reagent volume from a primary container, such as a reagent container, and its delivery to a secondary container, such as a reaction container. Under these conditions, a transport device brings the pipetting needle from one target position to the next. In each target position, the automatically controlled metering device effects the required removal or delivery of a liquid volume.

In the three-dimensional right-angled coordinate system of the transport device, the primary and secondary containers are disposed in container receptacles on carrier plates which are parallel to the XY-plane of the coordinate system. When the transport device brings the pipetting needle into a target position, the device first moves the pipetting needle in a plane parallel to the XY-plane until it is above the target container and then lowers the pipetting needle until it is in the correct position for withdrawal of liquid from a primary container or delivery of liquid to a secondary container.

To enable the transport device to bring the pipetting needle to an exact target position in the XY-plane, that is, exactly above a primary or secondary container, the following conditions should be met:

- the transport device control means should receive the X and Y coordinates of the target position as an input signal in order to be able to control the transport device appropriately,
- the primary and secondary containers should be at the exact position,
- the transport device should be adjusted in each transport direction, that is, each transport direction there should be a defined position applicable as a reference position.

Analyzer

FIG. 1 is a perspective view of an analyzer 11. The device comprises a horizontal baseplate 12, on which are disposed primary containers, such as sample containers 13 and reagent containers 23, and secondary containers, such as reaction containers 31. The analyzer 11 contains an automatic pipetting device, in which a pipetting needle 42 consists of an electrically conductive material connected to a metering device 96 by tubing 99. The metering device is preferably an automatically controlled metering syringe contained in the transport head 51 explained below.

A predetermined volume of liquid is transferred by the pipetting needle 42 from a primary container 13 or 23 to a secondary container 31. The pipetting device contains a transport device 51–55 for the controlled transport of the pipetting needle 42 in three directions at right angles to one another, the X, Y and Z directions. Two of the transport direction (X and Y), are horizontal, and the third direction (Z) is vertical. The transport device contains a transport head 51 which contains a drive 52 for transporting the pipetting needle 42 vertically. The transport head 51 preferably also contains a drive 53 for transporting a gripper 43 vertically. By means of this gripper, reaction containers can be transported to different processing positions, such as, from a loading position in which the reaction containers are charged with samples and reagents, to an incubator 36 contained in the analyzer, and from there to a washing device 62 also contained in the analyzer, or to a photometer 61.

The transport head 51 is movable by a suitable drive in the X direction along a rail 55. Rail 55 is movable by a suitable drive in the Y direction along rails 54 (see FIG. 2). Rails 54 are fixed on the baseplate 12.

The analyzer contains an electrically conductive reference body 45 rigidly connected to the baseplate 12 and having two outer surfaces 76, 77 and 78, 79, respectively, in each of the horizontal transport directions, (the X and Y directions), the outer surfaces being disposed perpendicularly to the direction of transport. The reference body 45 is used for the fine adjustment of the pipetting needle transport device 51–55 as described below. The reference body 45 is preferably a square bolt of square cross-section.

Figure 2:
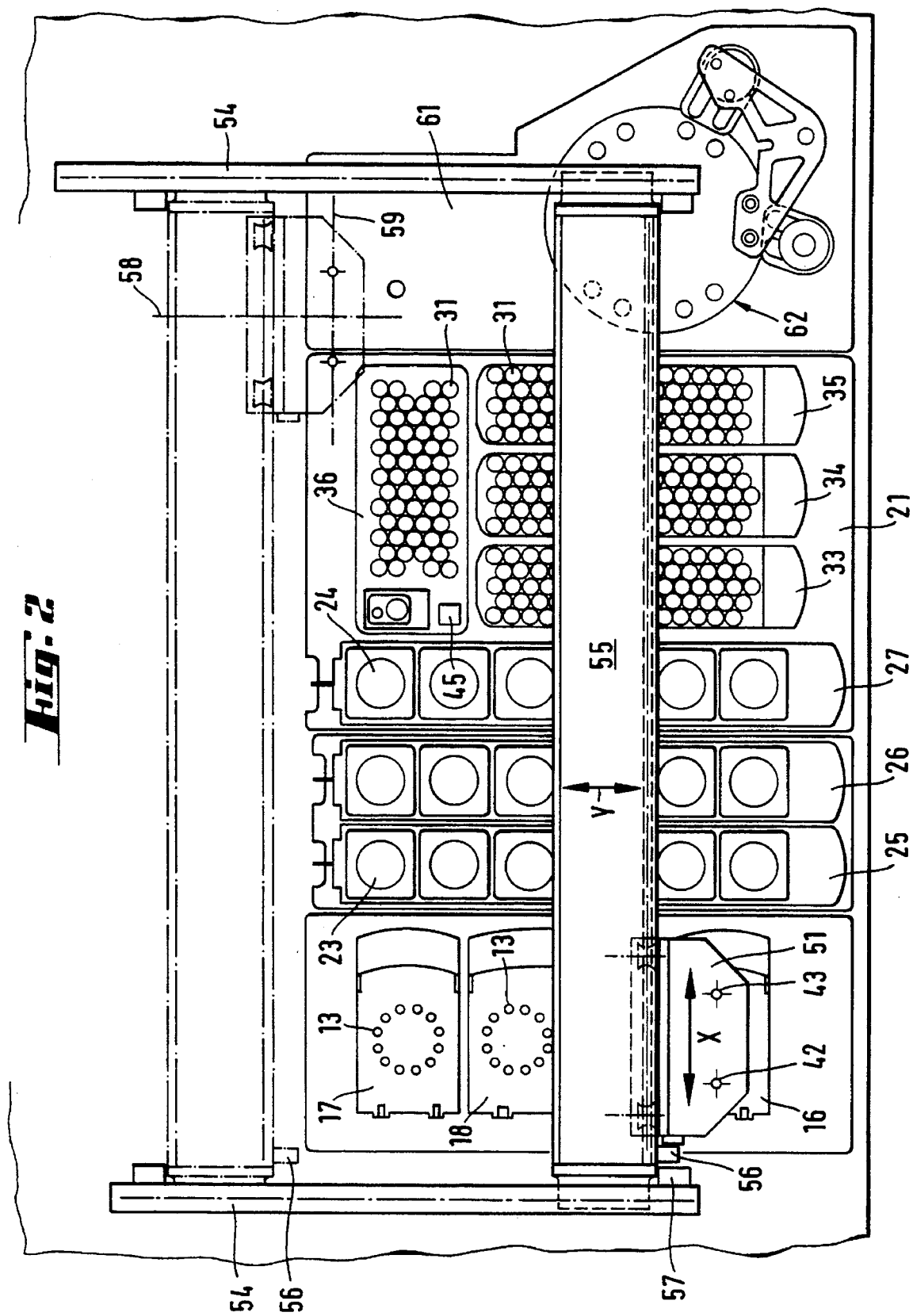
FIG. 2 is a plan view of the analyzer shown in FIG. 1.
Figure 3:
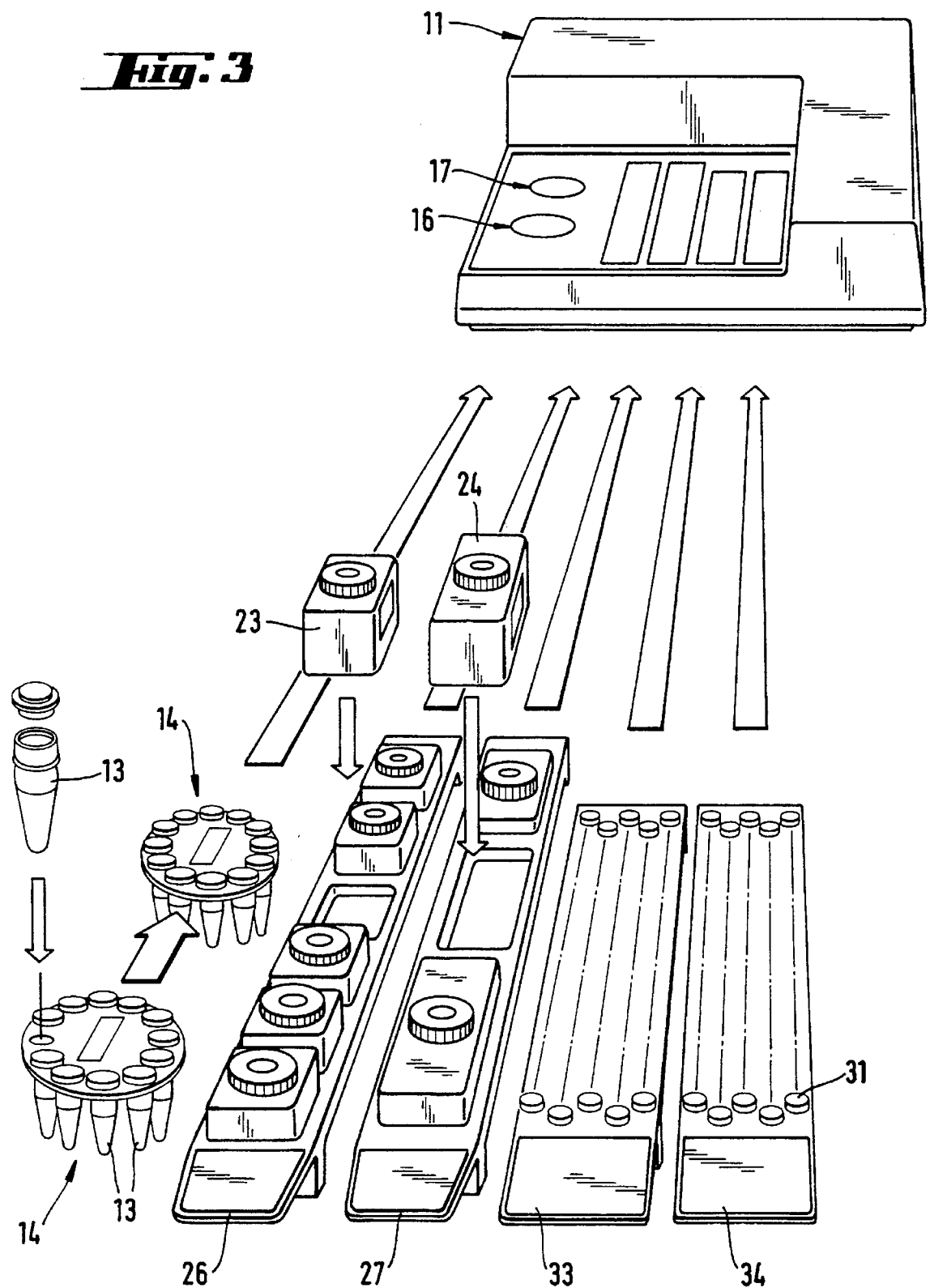
FIG. 3 is a perspective diagrammatic view of the arrangement of the sample containers, reagent containers and reaction containers in the analyzer 11.

A carrier plate 21 is disposed on the baseplate 12 and various containers are disposed thereon. As shown in FIGS. 1 to 3, the following containers, for example, are disposed on carrier plate 21:

sample containers 13 in sample container holders 16, 17, 18 which are in turn disposed in a sample container holder unit 15, reagent containers 23, 24 in reagent container holders 25, 26, 27, and reaction containers 31 in reaction container holders 33, 34, 35.

As shown in FIG. 3, the sample containers 13 can, for example, be disposed in a circular arrangement 14 received in one of the sample container holders. Each of the sample containers 13 has a lid which can be pierced by the pipetting needle. Each of the sample container holders 16, 17, 18 has a lid formed with apertures through which the pipetting needle has access to the sample container lids. The pipetting operations are performed with the sample containers closed.

As will be seen from FIG. 3, each of the reagent containers 23, 24 is closed by an appropriate lid. These lids can also be pierced by the pipetting needle. Thus, pipetting operations are performed with the reagent containers closed.

Figure 4:
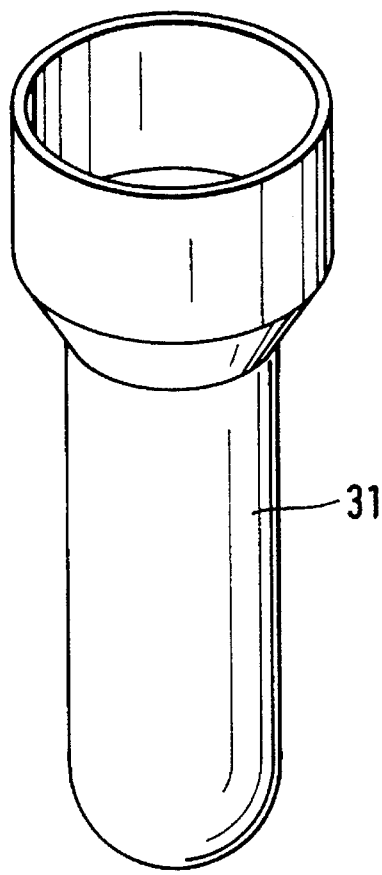
FIG. 4 is an enlarged perspective view of one of the reaction containers 31 in FIGS. 1–3.
Figure 5:
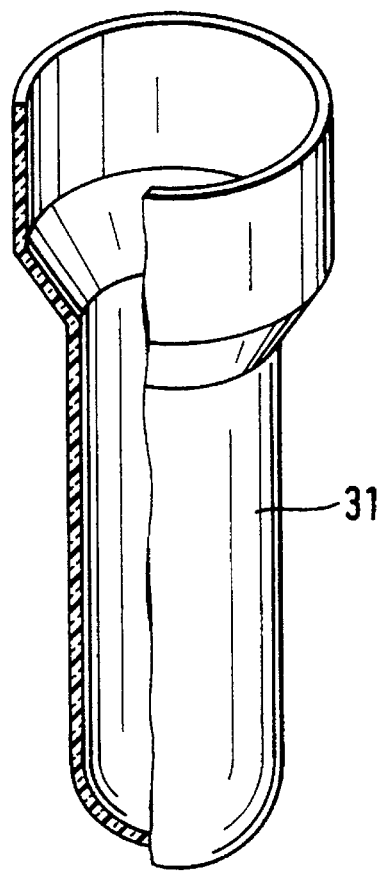
FIG. 5 is an illustration of the reaction container 31 of FIG. 4 showing the interior thereof.

FIG. 4 is an enlarged perspective view of one of the reaction containers 31 of FIGS. 1 to 3. FIG. 5 is an illustration of the reaction container 31 of FIG. 4 to show the interior of the reaction container.

Analyzer control Unit

All operations which are to be performed, including control of the metering device 96 and transport device 51–55, are controlled and coordinated by a central analyzer control unit (not shown). A control surface 64 or keyboard for inputting process parameters, and a display to display process states, are shown diagrammatically. The sample data applied to the sample tubes, for example, by bar coding, can be read into a memory via a manually held reading pen or scanner 63. Interfaces for a printer etc (not shown) are provided.

Means for adjusting the transport device 51–55

The embodiments of the analyzer 11 described below contain means for rough adjustment of the transport device 51–55 of the pipetting needle 42. For this purpose, for example, means are used by which the pipetting needle 42 is guided into an end position and the coordinates (Xe, Ye, Ze) of the end position of the pipetting needle in each of the three directions at right angles to one another are detected and stored. The end position of the pipetting needle 42 in the X and Y directions is defined by the corresponding end position of the transport head 51. FIG. 2 shows the transport head 51 in its end position in the X and Y directions. The end position of the transport head 51 in the X direction is detected by suitable means when the transport head 51 reaches the stop 56. The end position of the transport head 51 in the Y direction is detected by suitable means when the transport head 51 reaches the stop 57. The highest possible position of the pipetting needle permitted by its drive 52 defines the end position of the pipetting needle in the Z direction. The fact that the end position of the transport head 51 has been reached in each transport direction is detected by suitable means, such as, by an electric signal triggered by the contact between the transport head 51 and a stop and fed to the analyzer control unit.

The broken lines in FIG. 2 show the basic position 58 of the transport head 51 in the X direction and the basic position 59 of the rail 55 in the Y direction.

The analyzer 11 also contains the following means for fine (very accurate) adjustment of the transport device 51–55:

a circuit for measuring the electrical capacitance between the pipetting needle 42 and the reference body 45, and means for determining the coordinates of a reference position of the pipetting needle 42 in at least one of the horizontal transport directions, (X and Y), said means being adapted so to move the transport device 51–55 of the pipetting needle 42 so that the latter is moved in opposite directions in each case to a position near each of the two outer surfaces 76–79 of the reference body 45 which are disposed perpendicularly to the direction of transport, the pipetting needle 42 being moved in each case towards one surface of the reference member 45 until the value of the electrical capacitance between the pipetting needle 42 and the reference body 45 as measured by the circuit reaches a predetermined value corresponding to a specific distance between the pipetting needle 42 and the surface of the reference body 45.

Figure 6:
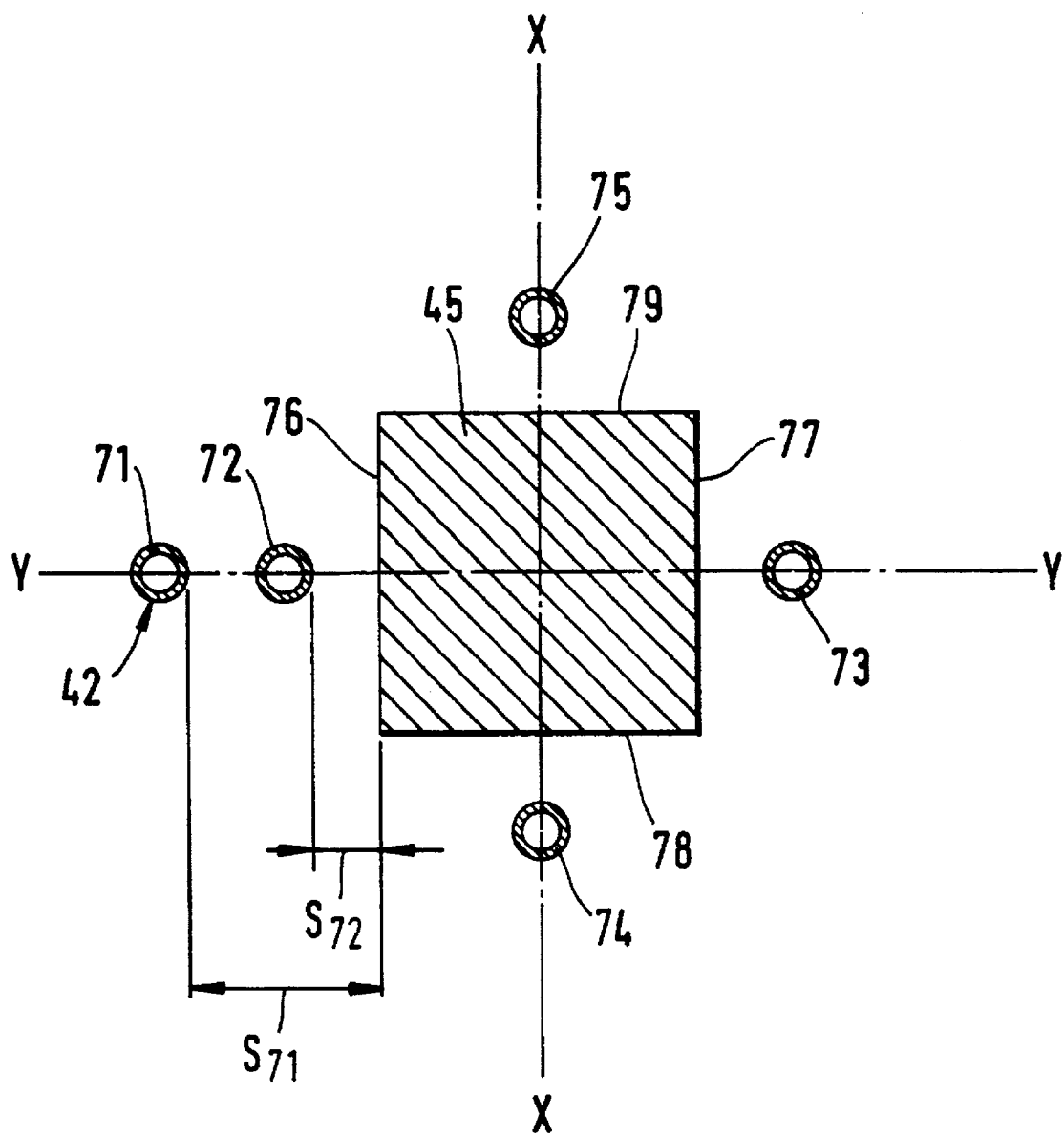
FIG. 6 is a diagram of the scanning of the reference body 45 by a pipetting needle 42.

As shown in FIG. 6, the scanned zone of the reference body 45 preferably has a square cross-section in a plane perpendicular to the longitudinal axis of the reference body 45.

The electrical resistance of the liquid contained in the tubing 99 connecting the pipetting needle 42 to the metering system 96 (see FIG. 9) is preferably larger than a predetermined limit.

1st preferred embodiment of the means for fine adjustment of the transport device 51–55.

A first preferred embodiment of the analyzer also contains the following means:

means for detecting and storing the coordinate values of the two thus defined positions of the pipetting needle 42 in the at least one horizontal transport direction, (X and/or Y), and, means for determining the coordinates of a reference position in the transport direction by calculating the average of the two coordinate values detected.

After the reference position coordinates have been determined, the X arid Y coordinates of all the pipetting positions of the pipetting needle with respect to the coordinates of the reference position are calculated in the above-mentioned control unit by reference to the relevant dimensions of the different parts of the analyzer.

2nd preferred embodiment of the means for fine adjustment of the transport device 51–55

A second preferred embodiment of the analyzer contains means for determining the coordinates Xo, Yo of a reference axis extending parallel to the vertical transport direction Z and through the reference body 45, said means being adapted so to move the transport device 51–55 of the pipetting needle 42 that the latter is moved in the two horizontal transport directions (X and Y directions) and in opposite directions in each case to a position near each of the two outer surfaces 76-79 of the reference body 45 which are disposed perpendicularly to the transport direction, the pipetting needle 42 being moved in each case towards a surface of the reference body 45 until the value of the electrical capacitance between the pipetting needle 42 and the reference body 45 as measured by the circuit reaches a predetermined value corresponding to a specific distance between the pipetting needle 42 and the surface of the reference body 45.

After the coordinates Xo, Yo of the above-mentioned reference axis have been determined, the X and Y coordinates of all the pipetting positions of the pipetting needle with respect to Xo, Yo are calculated in the abovementioned control unit by reference to the relevant dimensions of the different parts of the analyzer.

This second preferred embodiment preferably additionally contains the following means:

means for detecting and storing the coordinate values of the two thus defined positions of the pipetting needle 42 in each of the horizontal transport directions (X and Y directions), and means for determining the coordinate values of a reference position in each of the horizontal transport directions (X and Y directions) by calculating the average of the two detected coordinate values.

Figure 9:
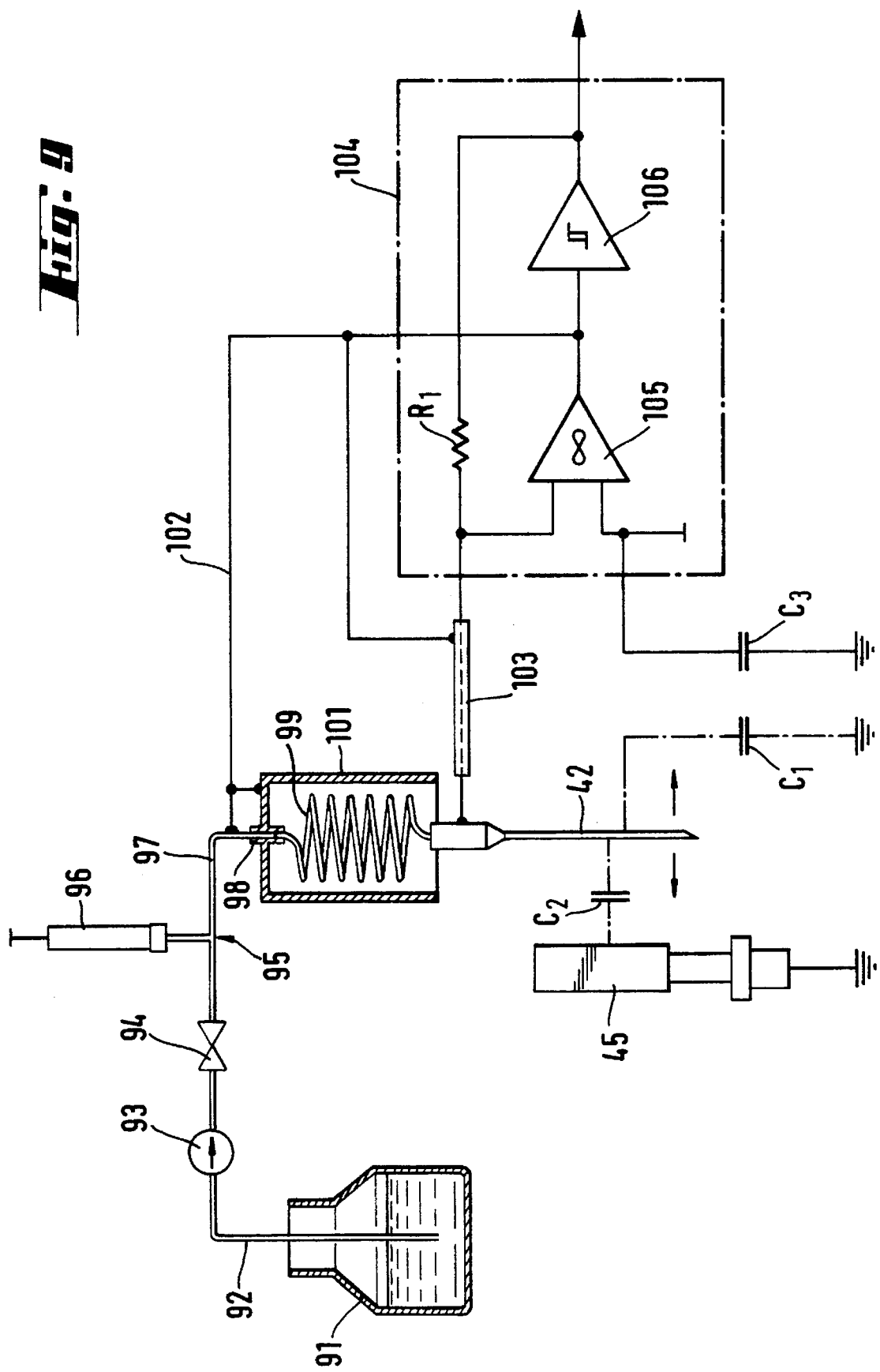
FIG. 9 is a diagram showing an arrangement for measuring the capacitance between the pipetting needle 42 and the reference body 45.
Figure 10:
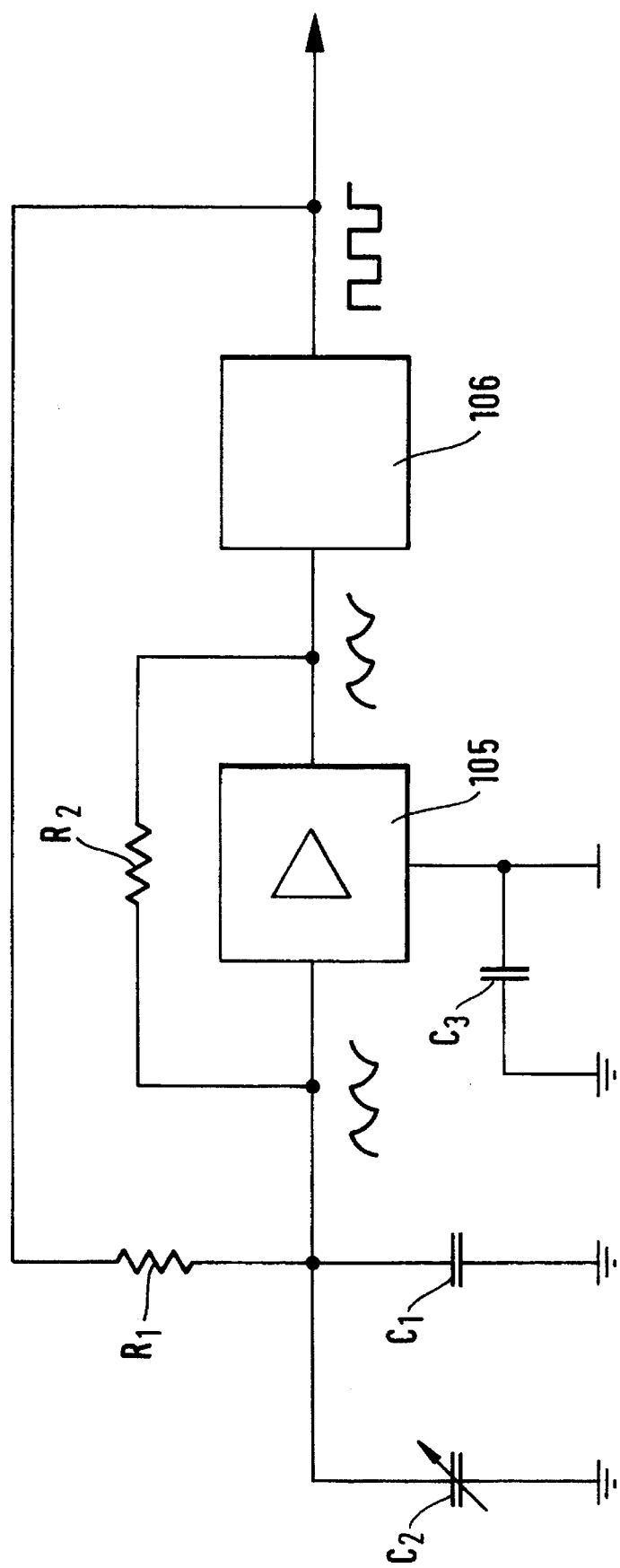
FIG. 10 is an equivalent circuit diagram of the arrangement shown in FIG. 9.
Figure 11:
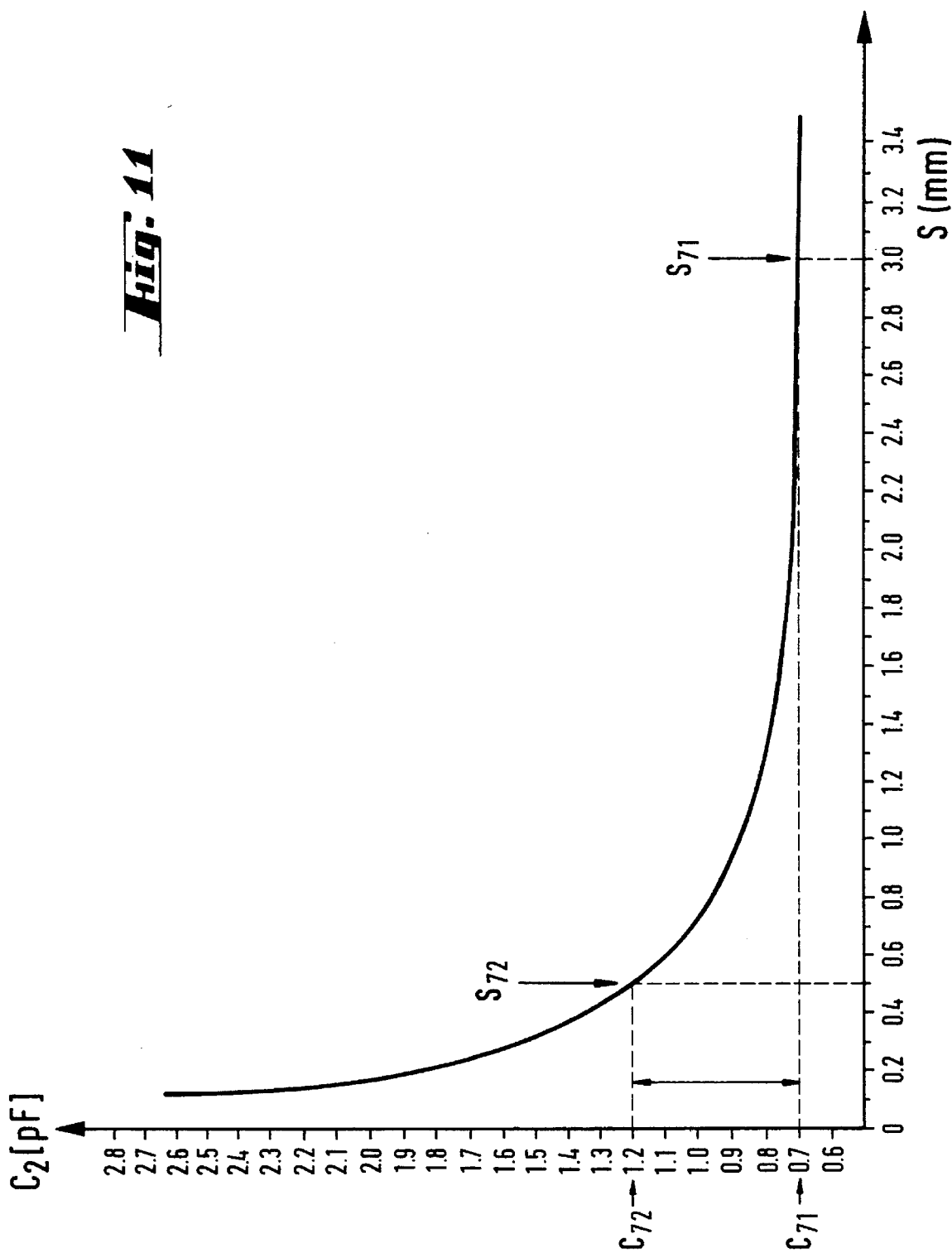
FIG. 11 is a diagram showing the variation of the electrical capacitance between the pipetting needle 42 and the reference body 45.

Circuit for measuring the capacitance between the pipetting needle and the reference body (FIGS. 9, 10 and 11)

A circuit, as shown in FIG. 9, is used to measure electrical capacitance between the pipetting needle 42 and the reference body 45. This circuit is also used in the analyzer as part of a level detector. A level detector is used to control the depth of immersion of the pipetting needle during pipetting operations (such as, on withdrawal of a sample volume from a sample container) by measuring the electrical capacitance between the pipetting needle and the surface of the liquid sample so that only a very short segment of the tip of the pipetting needle is immersed in the liquid sample. Thus, the amount of sample undesirably entrained at the outer surface of the pipetting needle is as small as possible. In addition to its own function as part of the pipetting device, the pipetting needle under these conditions has the additional function of being part of the electrical measuring circuit by means of which the electrical capacitance between the pipetting needle and the surface of the liquid sample is measured.

As will also be seen from FIG. 9, the pipetting needle 42 is in liquid connection with the liquid in a liquid container 91 via a tube 99, a connector 98 and a T-piece 95 having a metering syringe 96, and by a valve 94, a pump 93 and tubing 92. All these components form a liquid system which is filled with the liquid contained in the liquid container 91 during operation of the pipetting device. In the present exemplified embodiment, this liquid has good electrical conductivity.

Tube 99 is disposed in a guarding case 101. The connector 98 is mechanically and electrically connected to the case 101 and to the liquid in the tubing 97.

As will also be seen from FIG. 9, the pipetting needle 42 is electrically connected to the input of an oscillator circuit 104 by the internal conductor of a coaxial cable 103. The oscillator circuit 104 contains an impedance transformer 105 and a voltage comparator 106 connected thereto. A coupling resistor R1 connects the output of the voltage comparator 106 to the input of the impedance transformer 105. The electrical connection between the output of the impedance transformer 105 and the voltage comparator 106 is electrically connected to the outer conductor of the coaxial cable 103 and via a line 102 ("guard") to the guarding case 101 and to the liquid in the tubing 97. The guarding case 101 and the guard 102 serve for electrical decoupling of the circuit for measuring the capacitance C2 between the pipetting needle 42 and the reference body 45 from the above-mentioned pipetting device liquid system. In this way, the function of the circuit for measuring the capacitance C2 between the pipetting needle 42 and the reference body 45 is rendered insensitive to stray capacitances, which would otherwise influence the function of the measuring circuit by the mechanical and liquid connection of the pipetting needle 42 to the above-mentioned liquid system.

As shown diagrammatically in FIG. 9, the reference body 45 is mechanically and electrically connected directly to a baseplate 12 of the analyzer (see FIG. 1). The baseplate 12 is electrically grounded.

In FIG. 9, C2 represents capacitance between the pipetting needle 42 and the reference body 45. C3 represents capacitance between the oscillator circuit 104 and earth. In FIG. 10, C1 represents capacitance between the pipetting needle 42 and earth, when the pipetting needle is in a specific vertical position—such as, the position shown in FIG. 7—but so far away from the reference body 45 that C2 is practically zero. In the present example C1=4 picofarad.

FIG. 10 shows an equivalent circuit diagram of the arrangement shown in

FIG. 9. In FIG. 10, R2 represents the electrical resistance of the liquid in the tube 99 in FIG. 9.

FIG. 11 shows the variation of the capacitance C2 in picofarad as a function of the distance between the pipetting needle 42 and the reference body 45.

The oscillatory frequency f of the oscillator 104 is given by the following formula:

$$f=1/T=\frac{1}{2}*R1(C1+C2)$$

The oscillatory frequency f of the oscillator 104 is, for example, 120 kilohertz when R1=1 megaohm C1=4 picofarad and C2=0 picofarad.

Of course, f can have other values. Considerably higher values of f, for example in the megahertz range, are disadvantageous because the influence of interference signals becomes excessive. Considerably lower values of f are also disadvantageous because more time is required for evaluation of the oscillator circuit output signal.

FIG. 10 shows, among other things, the waveforms at three points of the equivalent circuit diagram of the oscillator circuit 104 according to FIG. 9. The waveform at the input and output of the impedance transformer 105 is due to the fact that the RC network of the oscillator circuit is continuously charged and discharged at a time constant t, where t=2* RI(C1+C2).

When the pipetting needle 42 approaches one of the lateral outside surfaces of the reference body 45, the value of C2 according to FIG. 11 increases and this results in a corresponding change of the value of f. By measuring the frequency f of the signal at the output of the voltage comparator 106 it is therefore possible to measure the value of C2 and hence determine the corresponding distance between the pipetting needle 42 and the outside side surfaces of the reference body 45. For this purpose, the value of C2 is first measured for a specific position of the pipetting needle 42 in the analyzer 11. This specific position of the pipetting needle is, for example, the position 71 shown in FIGS. 6 and 7, in which the distance S71 between the pipetting needle 42 and the reference body 45 is 3 millimeters. The corresponding value of C2 is given the reference C71 in FIG. 11.

For a suitable function of the impedance transformer 105 it is important that the resistance R2 of the liquid in the tube 99 should not drop below a present critical value of 100 kiloohm. Otherwise R2 would be too high a load on the impedance transformer 105. Too low a value of R2 may be due to the liquid in the liquid system of the pipetting device having a very low resistivity. By suitable choice of the parameters determining the value of R2, however, it is possible to obtain a value for this resistance to satisfy the above condition.

The value of R2 is given by $R2=r*1*4/(p\ d^2)$, where r=resistivity of the liquid in the tube 99 l=length of tube 99 d=inside diameter of tube 99

If r=0.26 ohm*meter, l=0.76 meter and d=0.76 mm,
  R2=263 kiloohm

Mode of operation of analyzer

With an analyzer, the pipetting needle 42 of the automatic pipetting device of the analyzer 11 is brought to a number of pipetting positions by means of a transport device 51–55, each pipetting position corresponding to the position of a specific container, the transport device 51–55 being adapted to move the pipetting needle 42 in three directions at fight angles to one another (X, Y and Z), each of these directions being parallel to one of the coordinate axes of the coordinate system of the transport device 51–55.

Before the fine adjustment of the pipetting needle transport device 51–55 as described below, rough adjustment thereof is carried out, for which purpose the pipetting needle 42 is brought by the transport device 51–55 to the above-defined end position in each of the three directions at right angles to one another and the coordinates (Xe, Ye, Ze) of the end position are detected and stored.

For fine (accurate) adjustment of the pipetting needle transport device 51–55, coordinates of reference points are determined. The electrically conductive reference body 45 is used for this purpose, and is rigidly connected to the baseplate 12 and has in each of the horizontal transport directions (X and Y directions) two outer surfaces 76–79, which are disposed perpendicularly to the transport direction.

For the fine (accurate) adjustment of the pipetting needle transport device 51–55, the following steps are carried out:

the electrical capacitance C2 between the pipetting needle 42 and the reference body 45 is measured with the above-described circuit, the value of C2 first being measured for a specific position 71 of the pipetting needle 42 in the analyzer 11. This specific position of the pipetting needle is, for example, the position 71 shown in FIGS. 6 and 7, in which the distance S71 between the pipetting needle 42 and the reference body 45 is 3 millimeters. The corresponding value of C2 is given the reference C71 in FIG. 11. As will be seen from FIG. 11, for example, C71 is 0.7 picofarad and to determine the coordinates of a reference position of the pipetting needle 42 in at least one of the horizontal transport directions (X and Y directions), the pipetting needle 42 is moved by the transport device 51–55 in opposite directions in each case to a position near each of the two outer surfaces 76, 77; 78, 79 of the reference body 45 which are disposed perpendicularly to the transport direction. In these conditions, the pipetting needle 42 is moved, for example, in the Y direction first towards an outer surface 76 of the reference body 45 until the pipetting needle reaches a position 72, in which the measured value of the electrical capacitance C2 between the pipetting needle 42 and the reference body 45 reaches a predetermined value C72 corresponding to a specific distance S72 between the pipetting needle 42 and the outer surface 76 of the reference body 45. The coordinate of the position 72 in the Y direction is Y72. This operation is then carried out in the opposite direction, that is, the pipetting needle 42 is moved in the Y direction towards a surface 77 of the reference body 45 until the pipetting needle reaches a position 73 in which the measured value of the electrical capacitance C2 between the pipetting needle 42 and the reference body 45 reaches a predetermined value C73 corresponding to a specific distance S73 between the pipetting needle 42 and the outer surface 77 of the reference body 45. The coordinate of the position 73 in the Y direction is Y73. In the context of the invention, C73 is preferably equal to C72 and S73 is equal to S72. As will be seen from FIG. 11, for example, C73=C72=1.2 picofarad.

Figure 7:
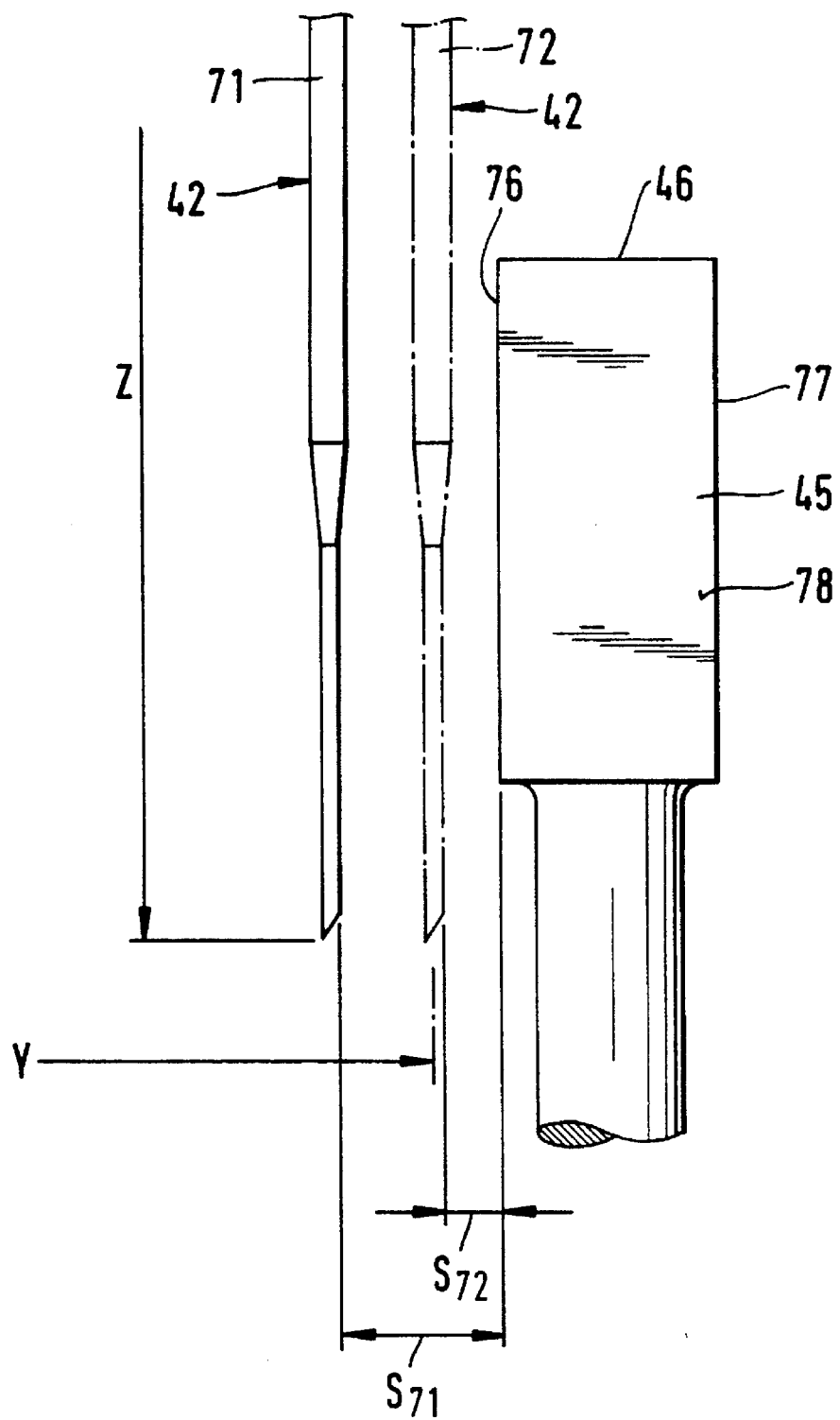
FIG. 7 is a diagram showing the movement of the pipetting needle 42 in a horizontal direction (X and Y directions) during the scanning operation shown in FIG. 6.
Figure 8:
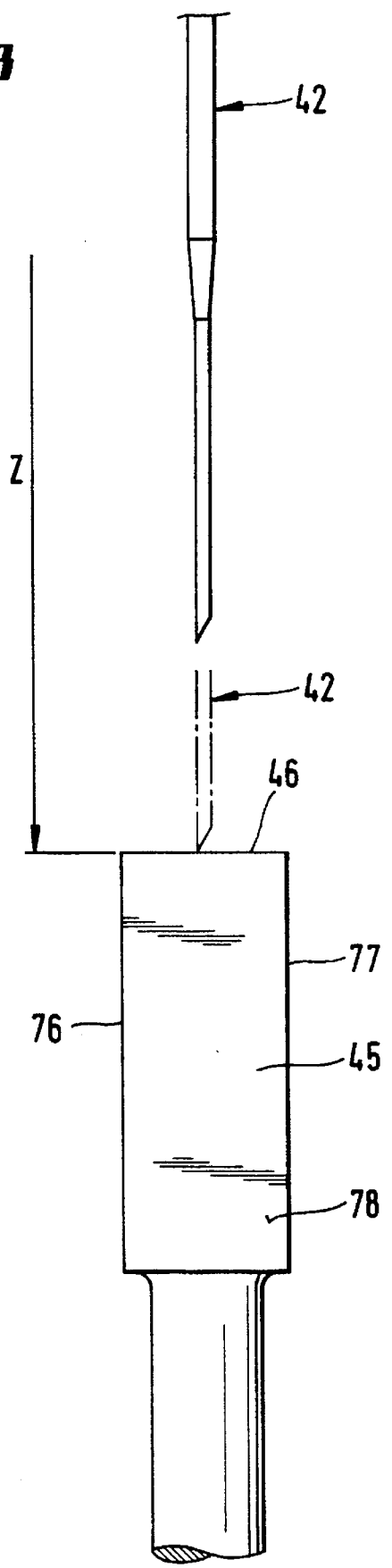
FIG. 8 is a diagram showing scanning in the vertical direction (Z direction) of the top surface of a reference body with a pipetting needle.

In the above-described method, and in the embodiments described below, the pipetting needle during its entire guided movement is situated against one of the lateral outside surfaces of the reference body 45 preferably in the vertical position (the Z direction) shown in FIG. 7, in which a considerable part of the pipetting needle lies opposite the outer surface. In this way, the capacitance C2 has a sufficiently high value. Also, as a result of the vertical position of the pipetting needle as shown in FIG. 7, adjustment accuracy is very high, particularly for the top part of the pipetting needle. This is a result of the adjustment the top part of the pipetting needle is positioned with the maximum accuracy at the different pipetting positions. The present exemplified embodiment affords the additional advantage that the gripper 43, carried and guided by the transport head 51, is also positioned with maximum accuracy at the different positions where it holds and moves the reaction containers 31.

After the determination of the coordinates of a reference position of the pipetting needle in the X and Y directions, including fine adjustment in at least one of the horizontal transport directions (X and Y directions), a reference position in the Z direction is defined in which the pipetting needle 42 is moved from its initial position in the highest position and with decreasing speed towards the center of the top surface 46 of the reference body 45 until the tip of the pipetting needle touches the surface 46 and this contact is detected by a suitable circuit. The reference position thus determined for the pipetting needle in the Z direction is stored.

1st preferred embodiment of the method for fine adjustment of the transport device 51–55

In a first preferred embodiment of the method for fine adjustment of the transport device 51–55, the coordinate values of the two thus defined positions of the pipetting needle 42 in the at least one horizontal transport direction are detected and stored. The coordinate values of a reference position in the at least one horizontal transport direction are determined by calculating the average of the two detected coordinate values, e.g. Y72 and Y73.

Determination of the positions 71 and 73 on opposite sides of the reference body 45 and the above-mentioned calculation of the average of the two detected coordinate values have the advantage that the symmetry of the reference body is thus utilized in order to eliminate the influence of any inaccuracies in the capacitance measurement on the calculated coordinate values of the reference position.

After the coordinates of the reference position have been determined, the X and Y coordinates of all the pipetting positions of the pipetting needle with respect to the coordinates of the reference position are calculated in the above-mentioned control unit by reference to the relevant dimensions of the different parts of the analyzer.

2nd preferred embodiment of the method for fine adjustment of the transport device 51–55

In a second preferred embodiment of the method for fine adjustment of the transport device 51–55, the coordinates Xo, Yo of a reference axis are determined, such axis extending parallel to the vertical transport direction (Z) and through the reference body 45. For this purpose, the pipetting needle 42 is moved by the transport device 51–55 in two horizontal transport directions (X and Y directions) in each case to a position near each of the two outer surfaces 76–79 of the reference body 45 which are disposed perpendicularly to the transport direction, the pipetting needle 42 being moved in each case towards one surface of the reference body 45 until the measured value of the electric capacitance between the pipetting needle 42 and the reference body 45 reaches a predetermined value corresponding to a specific distance between the pipetting needle 42 and the surface of the reference body 45.

Within the context of this method, for example, in addition to the above-described detection of specific reference points of the pipetting needle in the Y direction, the same method is performed in the X direction.

For this purpose, the pipetting needle is first moved towards a surface 74 of the reference body 45 until the measured value of the electrical capacitance between the pipetting needle 42 and the reference body 45 reaches a predetermined value C74 corresponding to a specific distance S74 between the pipetting needle 42 and the surface of the reference body 45, and this process is then performed in the opposite direction, that is the pipetting needle 42 is moved in the Y direction towards one surface 75 of the reference body 45 until the measured value of the electrical capacitance between the pipetting needle 42 and the reference body 45 reaches a predetermined value C75 corresponding to a specific distance S75 between the pipetting needle 42 and the surface of the reference body 45. Within the context of the invention, preferably, C74=C75=C73=C72 and S74=S75=S73=S72.

In this second preferred embodiment of the method for the fine adjustment of the transport device 51–55, the coordinate values of the two thus defined positions of the pipetting needle 42 in each of the horizontal transport directions are preferably detected and stored. The coordinate values of a reference position in each of the horizontal transport directions is determined by calculating the average of the two detected coordinate values.

After the coordinates Xo, Yo of the above-mentioned reference axis have been determined, the X and Y coordinates of all the pipetting positions of the pipetting needle with respect to Xo, Yo are calculated in the above-mentioned control unit by reference to the relevant dimensions of the different parts of the analyzer.

Arrangement for testing linearity of the pipetting needle

Irrespective of the apparatus and method used for accurate adjustment of the pipetting needle transport device, the above-described analyzer comprises an arrangement which allows the linearity of the pipetting needle to be tested. The arrangement comprises the following means:

means for guiding the tip of the pipetting needle 42 around the periphery of the top edge of a reference body 45, the tip of the pipetting needle 42 being guided at a specific distance d from the top edge, which distance is a measure of the acceptable curvature of the pipetting needle, an electrical circuit for detecting electrical contact between the tip of the pipetting needle and the reference body 45, and a display connected to this circuit, to display unacceptable curvature of the pipetting needle in response to an output signal from the circuit detecting electrical contact between the tip of the pipetting needle 42 and the reference body 45.

This arrangement is preferably used in combination with the above-described means for adjusting the transport device 51–55 of the pipetting needle 42.

Method of testing the linearity of the pipetting needle

Figure 12:
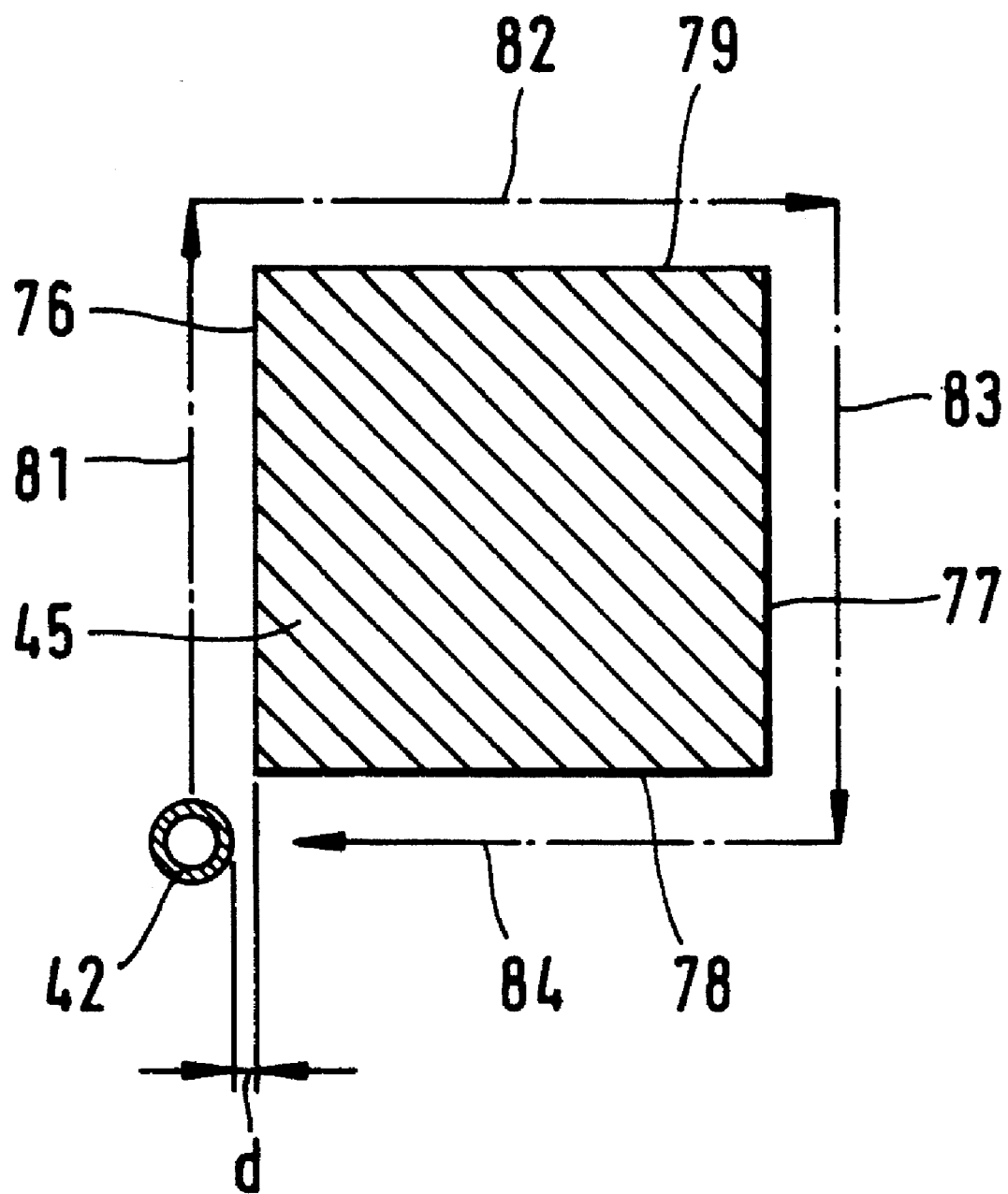
FIG. 12 is a diagram showing the guidance of a pipetting needle 42 according to the invention around a reference body 45 for the purpose of testing the linearity of the pipetting needle.
Figure 13:
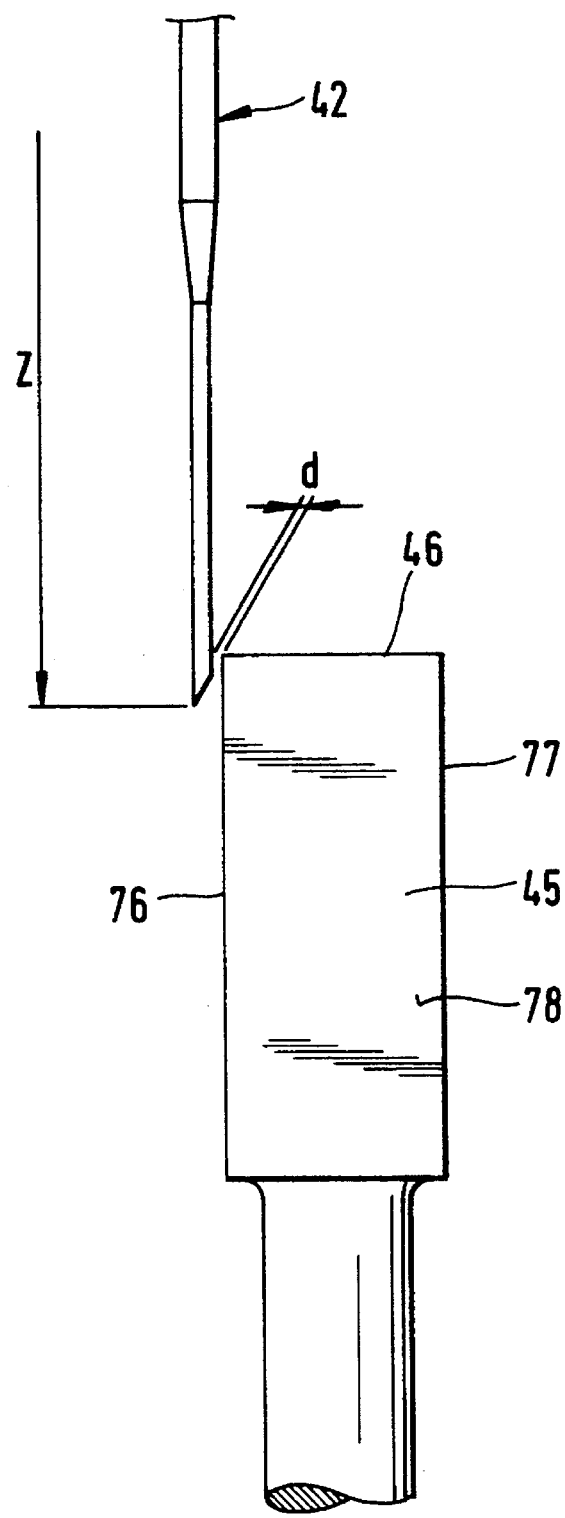
FIG. 13 is a diagram showing the position of the pipetting needle 42 in the vertical direction (Z direction) during the guidance of the pipetting needle 42 around the reference body 45 as shown in FIG. 12.

After accurate adjustment of the transport device 51–55 of the pipetting needle 42, which is preferably carried out with the above-described method, the linearity of the pipetting needle 42 is tested by the following method. As shown in FIGS. 12 and 13, the tip of the pipetting needle 42 is guided around the periphery of the top edge of a reference body 45 along a path 81, 82, 83, 84, the tip of the pipetting needle 42 being guided at a specific distance d from the edge of the reference body 45, which distance is a measure of the acceptable curvature of the pipetting needle. The distance d is, for example, 0.45 mm. The vertical position of the pipetting needle with respect to the reference body is as shown in FIG. 13. Any contact between the reference body 45 and the pipetting needle 42 is detected by an electrical circuit which in such a case results in the display of an unacceptable curvature of the pipetting needle.

Upon reading the present specification, various alternative embodiments will become obvious to those skilled in the art. For example, sizes and shapes of various components may be employed to achieve the stated objectives. These variations are to be considered within the scope and spirit of the invention, which is only to be limited by the claims which follow and their equivalents.

What is claimed is:

1. An analyzer comprising:
   a) a horizontally disposed baseplate on which primary containers and secondary containers are disposed;
   b) a metering device for measuring a predetermined volume of a liquid;
   c) a pipetting needle for transferring a predetermined volume of liquid from a primary container to a secondary container, the pipetting needle being formed of an electrically conductive material and being connected by tubing to the metering device;
   d) a transport device for the controlled transport of the pipetting needle in three directions at right angles to one another, two of the transport directions extending horizontally and the third transport direction extending vertically;
   e) an electrically conductive reference body having a top edge and being positioned at a predetermined location with respect to the analyzer; and
   f) a control device for controlling the metering device and the transport device, the control device comprising:
      1) means for guiding the tip of the pipetting needle around the the external periphery of the top edge of the reference body, the tip of the pipetting needle being guided at a specific distance from the top edge of the reference body, the distance being a measure of the acceptable curvature of the pipetting needle, and
      2) an electrical circuit between the pipetting needle and the reference body for detecting an electrical contact between the tip of the pipetting needle and the reference body.

2. The analyzer according to claim 1, wherein the electrically conductive reference body is rigidly connected to the baseplate, and in each of the horizontal transport directions has two outer surfaces disposed perpendicularly to the transport direction.

3. The analyzer of claim 2 further comprising means for determining the coordinates of a reference position of the pipetting needle in at least one of the horizontal transport directions, the means being adapted to move the transport device of the pipetting needle causing the pipetting needle to be moved in opposite directions in each case to a position near each of the two outer surfaces of the reference body which are disposed perpendicularly to the transport direction, the pipetting needle being moved in each case towards a surface of the reference body until the value of the electrical capacitance between the pipetting needle and the reference body, as measured by a circuit, reaches a predetermined value corresponding to a specific distance between the pipetting needle and the surface of the reference body.

4. The analyzer according to claim 1, wherein the reference body is in the form of a parallelopiped.

5. The analyzer according to claim 1, wherein the top edge of the reference body is shaped as a square.

* * * * *